United States Patent
Keller

(10) Patent No.: US 9,918,877 B2
(45) Date of Patent: Mar. 20, 2018

(54) WELDING HELMET BOX

(71) Applicant: Lincoln Global, Inc., City of Industry, CA (US)

(72) Inventor: Timothy Keller, Painesville, OH (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 98 days.

(21) Appl. No.: 15/073,826

(22) Filed: Mar. 18, 2016

(65) Prior Publication Data

US 2017/0112218 A1 Apr. 27, 2017

Related U.S. Application Data

(60) Provisional application No. 62/246,694, filed on Oct. 27, 2015.

(51) Int. Cl.
| | | |
|---|---|---|
| *A45C 11/02* | (2006.01) | |
| *A61F 9/06* | (2006.01) | |
| *B65D 5/42* | (2006.01) | |
| *B65D 5/50* | (2006.01) | |
| *B65D 85/18* | (2006.01) | |

(52) U.S. Cl.
CPC .............. *A61F 9/06* (2013.01); *B65D 5/4204* (2013.01); *B65D 5/505* (2013.01); *B65D 85/18* (2013.01)

(58) Field of Classification Search
CPC ......... A45C 11/02; A45C 13/02; A42B 3/006; A61F 9/06; B65D 77/26; B65D 85/18
USPC ............. 206/297; 190/13 F; 229/162.6, 915, 229/120.32, 120.33, 120.37, 120.38, 122, 229/122.21, 162.1; 211/33
See application file for complete search history.

(56) References Cited

U.S. PATENT DOCUMENTS

| | | | | |
|---|---|---|---|---|
| 1,771,706 | A | * | 7/1930 | Cavanagh ................ B65D 5/38 206/8 |
| 2,122,714 | A | * | 7/1938 | Callahan ................ B65D 25/22 206/8 |
| 2,162,089 | A | * | 6/1939 | Kagen .................. B65D 5/0254 206/777 |
| 2,343,128 | A | * | 2/1944 | Anderson .............. A45C 11/02 206/8 |

(Continued)

FOREIGN PATENT DOCUMENTS

| | | |
|---|---|---|
| CN | 204776437 U | 11/2015 |
| DE | 20 2007 012 114 U1 | 11/2007 |
| FR | 2763563 A1 | 11/1998 |

OTHER PUBLICATIONS

"Speedglas 100 3M Welding Helmet", can be located on the Internet at: http://www.usedsurrey.com/classified-ad/Speedglas-100-3M-welding-helmet-BLACK_22446965, accessed on Dec. 22, 2015.

(Continued)

*Primary Examiner* — Sue A Weaver
(74) *Attorney, Agent, or Firm* — Brad C. Spencer

(57) ABSTRACT

Provided is a container for a welding helmet. The container includes an outer box and a removable insert wedge that is removable from the outer box. The removable insert wedge includes a tongue portion, extending through a headband of the welding helmet, and attached to the welding helmet. The outer box forms an opening in at least one vertical side of the outer box, thereby enabling the welding helmet and a lens of the welding helmet to be accessed from outside of the outer box through the opening. The opening is sized to prevent removal of the insert wedge and attached welding helmet through the opening without damaging the outer box.

18 Claims, 4 Drawing Sheets

(56) References Cited

U.S. PATENT DOCUMENTS

| | | | | |
|---|---|---|---|---|
| 2,496,619 | A * | 2/1950 | Cunningham, Jr. | B65D 5/38 206/8 |
| 4,925,087 | A | 5/1990 | Ostrander | |
| 5,303,829 | A * | 4/1994 | Kennedy | A47F 7/06 211/30 |
| 5,624,041 | A * | 4/1997 | Van Druff, Jr. | A47F 7/06 211/30 |
| 8,701,954 | B1 * | 4/2014 | Weinmeister | B60R 7/10 206/8 |
| 2008/0289974 | A1 * | 11/2008 | McClore | A45C 11/02 206/8 |
| 2011/0219506 | A1 * | 9/2011 | Uttrachi | A61F 9/067 2/8.6 |
| 2015/0320181 | A1 * | 11/2015 | Moncada | A45C 13/08 224/153 |
| 2016/0101926 | A1 * | 4/2016 | Tseng | B65D 85/18 206/8 |

OTHER PUBLICATIONS

"CCM 7000 Ice HOckey Goalie Mask", can be located on the Internet at: http://www.ebay.com/itm/CCM-7000-Ice-Hockey-Goalie-Mask-NEW-JR-SR-BLACK-WHITE-Helmet-Roller-Inline-/261416363032, accessed on Dec. 22, 2015.

"Unique Try-On Helmet Packaging", can be located on the Internet at: http://craig-ccdesign.blogspot.in/2012/02/blog-post.html, accessed on Dec. 22, 2015.

"Star Wars Stormtrooper Collectors Helmet", can be located on the Internet at: http://themovieandtvstore.com/star-wars-stormtrooper-collectors-helmet.html, accessed on Dec. 22, 2015.

"New Reebok 3K Helmet Xs Black", can be located on the Internet at: http://www.ebay.com/itm/New-Reebok-3K-Helmet-Xs-Black-/172036322014, accessed on Dec. 22, 2015.

"CCM Resistance Helmet", can be located on the Internet at: http://www.kijiji.ca/v-hockey/markham-york-region/ccm-resistance-helmet/1144585297?enableSearchNavigationFlag=true, accessed on Dec. 22, 2015.

"Decorated Corrugated Fibreboard", can be located on the Internet at: http://www.pac.ca/2007-packaging-competition-winners.html, accessed on Dec. 22, 2015.

"Dots Helmet", can be located on the Internet at: http://www.cyclestyle.com.au/product/dots-helmet/, accessed on Dec. 22, 2015.

"Bell Super Helmet", can be located on the Internet at: http://singletrackworld.com/forum/topic/bell-super-helmet-first-impressions, accessed on Dec. 22, 2015.

"Easton Hockey Helmet Packaging", can be found on the Internet at: http://www.elibclarkdesign.com/graphic/easton-hockey-helmet-packaging, accessed on Dec. 22, 2015.

"Evade Aero Road Bicycle Helmet", can be found on the Internet at: http://www.ebay.com/bhp/specialized-helmet, accessed on Dec. 22, 2015.

* cited by examiner

WELDING HELMET BOX

CROSS-REFERENCE TO RELATED APPLICATIONS

Benefit of U.S. Provisional Patent Application Ser. No. 62/246,694, filed Oct. 27, 2015, is hereby claimed and the disclosure incorporated herein by reference.

BACKGROUND OF THE INVENTION

Field of the Invention

The present invention relates to packaging for helmets, in particular to a box for a welding helmet for storing the welding helmet prior to purchase and use by a consumer.

Description of Related Art

It is known to provide packaging for a welding helmet, for storing the welding helmet prior to a retail sale and subsequent use by a welder. For example, a welding helmet can be stored in a sealed plastic container to protect the helmet and lens prior to sale.

BRIEF SUMMARY OF THE INVENTION

The following summary presents a simplified summary in order to provide a basic understanding of some aspects of the devices and systems discussed herein. This summary is not an extensive overview of the devices and systems discussed herein. It is not intended to identify critical elements or to delineate the scope of such devices and systems. Its sole purpose is to present some concepts in a simplified form as a prelude to the more detailed description that is presented later.

In accordance with one aspect, provided is a container for a welding helmet. The container includes an outer box and a removable insert wedge that is removable from the outer box. The removable insert wedge includes a tongue portion, extending through a headband of the welding helmet, and attached to the welding helmet. The outer box forms an opening in at least one vertical side of the outer box, thereby enabling the welding helmet and a lens of the welding helmet to be accessed from outside of the outer box through the opening. The opening is sized to prevent removal of the insert wedge and attached welding helmet through the opening without damaging the outer box.

In accordance with another aspect, provided is a container for a welding helmet. The container includes an outer box and a removable insert wedge that is removable from the outer box. The removable insert wedge comprises a tongue portion extending through a headband of the welding helmet. The insert wedge includes respective slots adjacent to the tongue portion that allow the headband to project into the insert wedge beneath the tongue portion. The tongue portion is attached to the headband. The insert wedge forms a central depression for nesting the welding helmet within the insert wedge. A forwardly-projecting spatter guard on the welding helmet projects beneath an upper surface of the insert wedge when the welding helmet is nested within the insert wedge. The outer box forms an opening in at least one vertical side of the outer box, thereby enabling the welding helmet and a lens of the welding helmet to be accessed from outside of the outer box through the opening. The opening is sized to prevent removal of the insert wedge and attached welding helmet through the opening without damaging the outer box.

In accordance with another aspect, provided is a container for a welding helmet. The container includes an outer box comprising a hinged access panel, an insert wedge that is removable from the outer box, and a helmet attachment tongue extending from the insert wedge. The helmet attachment tongue has a proximal end attached to the insert wedge and a distal end. The welding helmet comprises a headband that is rotatable within the welding helmet to a storage position. With the headband in the storage position, the helmet attachment tongue extends through the headband and is folded upward to extend along a central region enclosed by the headband. The distal end of the helmet attachment tongue is tied to the headband at an upper portion of the welding helmet. The insert wedge includes respective slots adjacent to the proximal end of the helmet attachment tongue. A lower portion of the headband projects into the insert wedge through the respective slots and beneath the helmet attachment tongue. The insert wedge forms a central depression for nesting the welding helmet within the insert wedge, and a forwardly-projecting spatter guard on the welding helmet projects beneath an upper surface of the insert wedge when the welding helmet is nested within the insert wedge. The central depression is formed by a cut portion, in the upper surface of the insert wedge, that is folded inwardly into the insert wedge. The outer box forms an opening in at least one vertical side of the outer box, thereby enabling the welding helmet and a lens of the welding helmet to be accessed from outside of the outer box through the opening. The opening is sized to prevent removal of the insert wedge and attached welding helmet through the opening without damaging the outer box. The welding helmet and attached insert wedge are removable from the outer box without damaging the outer box when the access panel is in an open position.

DETAILED DESCRIPTION OF THE INVENTION

Figure 1:
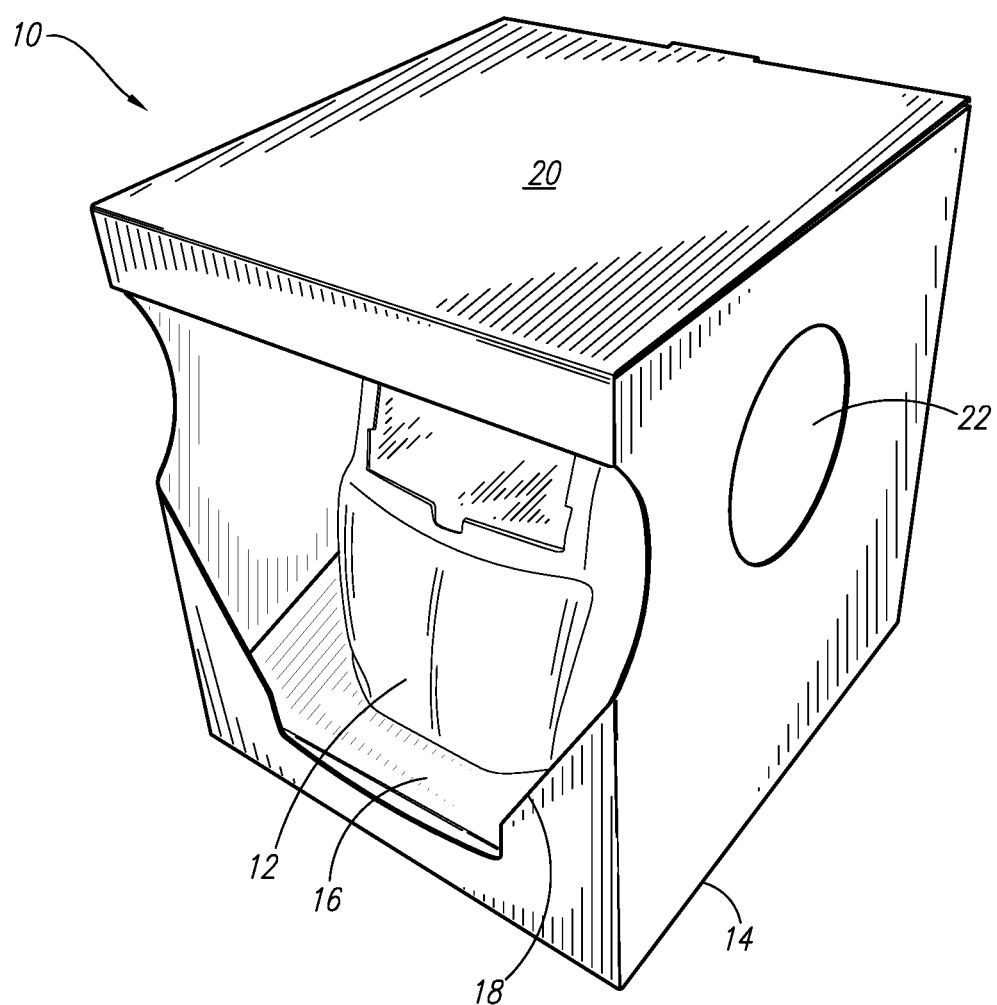
FIG. 1 is a perspective view of a container for a welding helmet.

Embodiments of the present invention relate to a container or packaging (e.g., a storage box) for a welding helmet. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

FIG. 1 provides a perspective view of an example packaging or container 10 for storing a welding helmet 12 prior to purchase and use by a consumer. The container 10 can be constructed from a material that can be cut and folded into a desired shape from flat stock (e.g., cardboard), or the container can be constructed from other suitable materials (e.g., plastic). However, for ease of explanation, the container 10 will be discussed in the context of a cardboard box.

Cardboard boxes can typically be readily opened, or broken into by cutting or tearing the cardboard material. The container 10 discussed herein includes several security features that inhibit the removal of the welding helmet 12 from the container, to reduce the likelihood that the helmet is stolen at a point of sale (e.g., a retail store). That is, the security features intentionally make it difficult to remove the welding helmet from the container 10 without damaging the container.

The container 10 has a two-piece design comprising an outer box 14 and a removable inset wedge 16 to which the welding helmet 12 is attached. The insert wedge 16 sits inside of the outer box 14 at the bottom of the box and forms a nest for securing the welding helmet 12 upright within the box. The outer box 14 has a large, frontward facing opening 18 in the front vertical side of the box. The opening 18 allows the welding helmet 12 and its attached filter or lens to be viewed and touched without opening the outer box 14. The opening 18 enables the welding helmet 12 and lens to be accessed from outside of the outer box 14 (e.g., for inspection prior to purchase) through the opening, without requiring the outer box itself to be opened and the welding helmet removed.

The top of the box forms a hinged access panel 20 through which the helmet 12 and attached insert wedge 16 can be removed from the outer box 14. The hinge can be located along the front edge of the top surface of the box 14, or along a lateral edge if desired. The edge opposite the hinge can include a conventional insert tab for locking the access panel 20 closed. If desired, the edges of the top of the outer box 14 around the access panel 20 can be sealed closed, such as by taping, gluing, etc.

One security feature of the container 10 lies in the size of the frontward facing opening 18 with respect to the insert wedge 16 and attached welding helmet 12. The welding helmet 12 and insert wedge 16 cannot be removed through the frontward facing opening 18 without damaging (e.g., tearing) the outer box 14 or otherwise enlarging the opening. Forward movement of the front of the insert wedge 16 is limited by the lower perimeter of the frontward facing opening 18, and when the insert wedge and helmet 12 are tipped forward within the box, the helmet would strike the top of the box (i.e., the hinged access panel 20). Thus, there is very little available movement for the insert wedge 16 and welding helmet 12 within the outer box 14 when the access panel 20 is in a closed position. When the access panel 20 is in an open position, the insert wedge 16 and helmet 12 can be removed together vertically from the outer box 14 without damaging the outer box.

Figure 2:
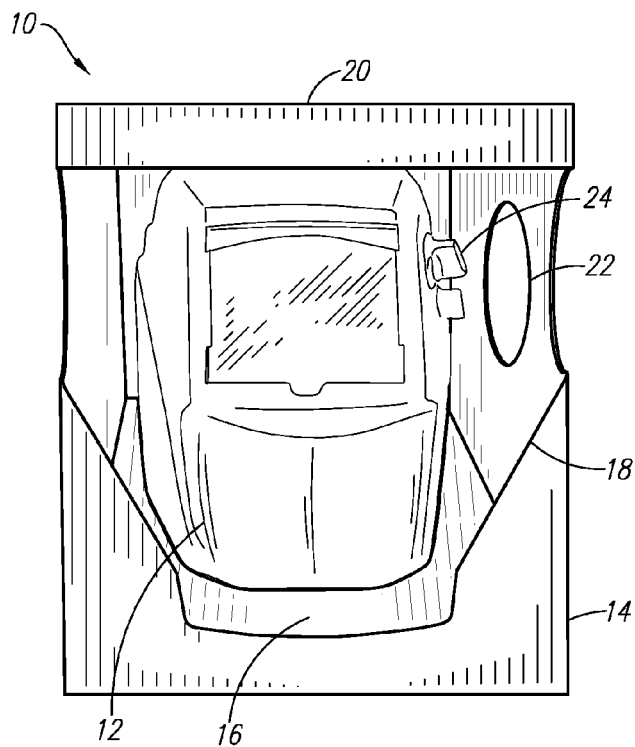
FIG. 2 is a front elevation view of a container for a welding helmet.

FIG. 2 provides a front elevation view of the outer box 14, insert wedge 16 and welding helmet 12. Information can be printed on the exterior surface of the storage box, such as information regarding the shade, lens type, viewing area, speed, etc. It can be seen that lower portions of the welding helmet 12 are recessed or nested within the insert wedge 16.

The insert wedge 16 has a central opening or depression that allows the welding helmet 12 to nest within the insert wedge.

Figure 3:
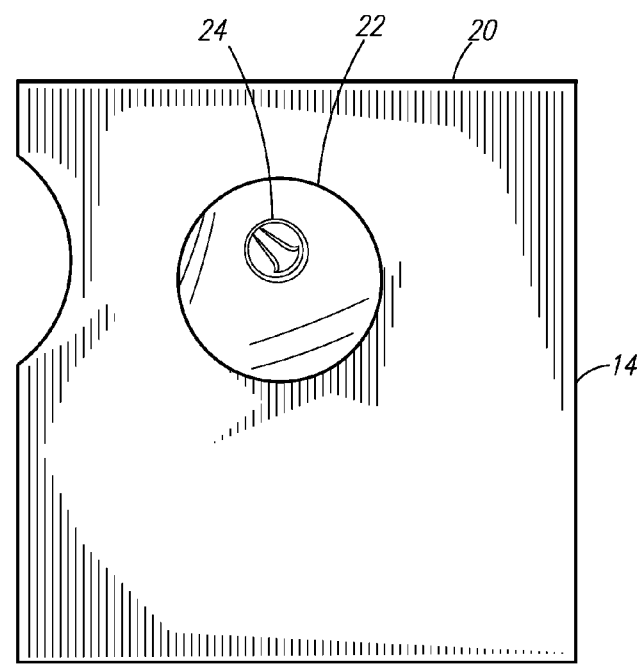
FIG. 3 is a side elevation view of a container for a welding helmet.

FIG. 3 provides side elevation view of the outer box 14 and a portion of the welding helmet 12. The outer box 14 can include an opening 22 that is aligned with a shade adjustment knob 24 for the lens. The shade adjustment knob 24 adjusts the shade setting of the lens. The opening 22 allows the shade adjustment knob 24 to be accessed from outside of the outer box 14. Information about the welding helmet and lens can be printed on any of the surfaces of the outer box 14, such as the side surface shown in FIG. 3. The outer box 14 can, but need not, have a symmetrical configuration. For example, only one side of the outer box 14 may have the opening 22 for accessing the shade adjustment knob 24, since a welding helmet will typically only have one shade adjustment knob 24 located on one side of the welding helmet.

Figure 4:
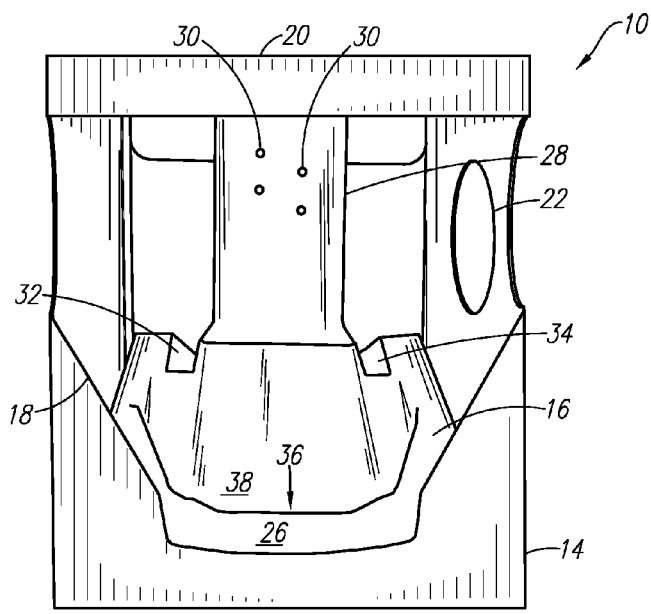
FIG. 4 is another front elevation view of a container for a welding helmet.

FIG. 4 provides a front elevation view of the container 10 with the helmet removed. The outer box 14 and insert wedge 16 are shown. The insert wedge 16 is generally wedge shaped and has an angled upper surface 26 that rises from the front of the box 14 toward the rear of the box. Along the rear vertical wall of the outer box 14 is a tongue portion 28 or helmet attachment tongue of the insert wedge 16. At a proximal end of the tongue portion 28, the tongue portion 28 is attached to and folded upward from the main body of the insert wedge 16 and projects upward within the outer box 14. The tongue portion 28 is attached to the welding helmet when the helmet is stored in the box. The tongue portion 28 can include one or more apertures 30 that allow the tongue portion (and, thus, the insert wedge 16) to be tied to the welding helmet. For example, the tongue portion 28 can be tied to the headgear of the helmet via suitable wire ties, strings, etc. The apertures 30 can be located at a distal end of the tongue portion 28 as shown, or in a more central location between the proximal and distal ends of the tongue. The ability to tie the tongue portion 28 to the welding helmet itself is another security feature of the container 10.

Figure 5:
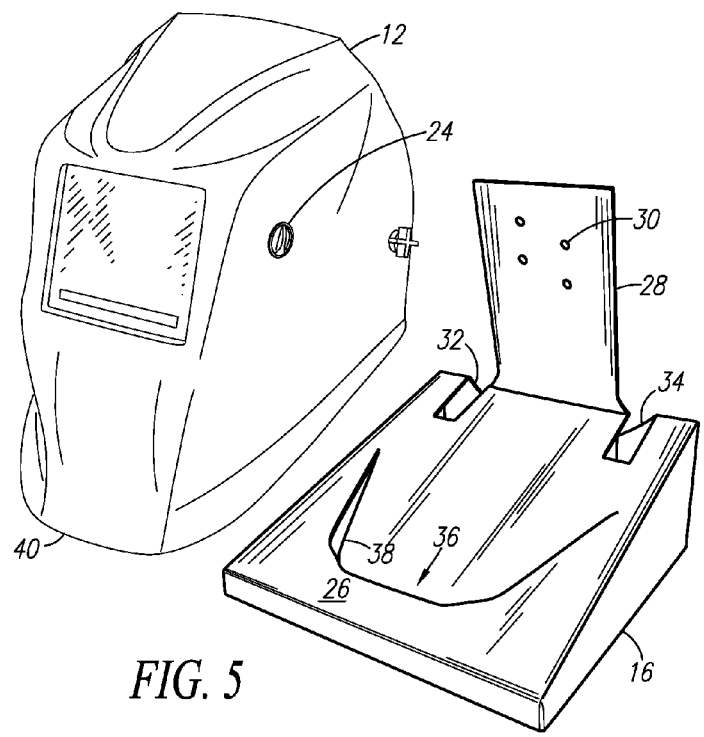
FIG. 5 is a perspective view of a portion of a container for a welding helmet alongside the welding helmet.

A perspective view of the insert wedge 16 is provided in FIG. 5. Respective slots 32, 34 or openings in the insert wedge 16 are provided on both sides of the tongue portion 28 at the proximal end of the tongue portion, and the upward fold in the tongue portion is located generally between the slots. The slots 32, 34 accommodate the headgear of the welding helmet, as will be discussed below, and allow the tongue portion to be inserted through the headgear.

The central depression 36 in the insert wedge 16 for nesting the welding helmet 12 inside of the wedge can be seen in FIGS. 4 and 5. The central depression 36 can be formed by cutting or slitting the wedge 16 to form a large hinged flap 38 and slightly folding the flap downwards into the interior volume of the wedge. The hinged flap 38 will thus have a slightly steeper slope than the upper surface 26 of the insert wedge 16. The lower front portion of the welding helmet 12 forms a forwardly-projecting spatter guard 40 or neck protector. When placed into the insert wedge 16, the spatter guard 40 will project forward beneath the upper front surface of the insert wedge 16. This helps to lock the welding helmet 12 in place within the insert wedge 16 and acts an additional security feature. If the welding helmet 12 is lifted vertically or rotated rearward, the spatter guard 40 will catch on the front portion of the insert wedge 16. In order to remove the welding helmet when it is untied from the insert wedge 16, the top of the box is opened such that the welding helmet can be rotated forwardly to thereby remove the neck protector from the insert wedge.

Figure 6:
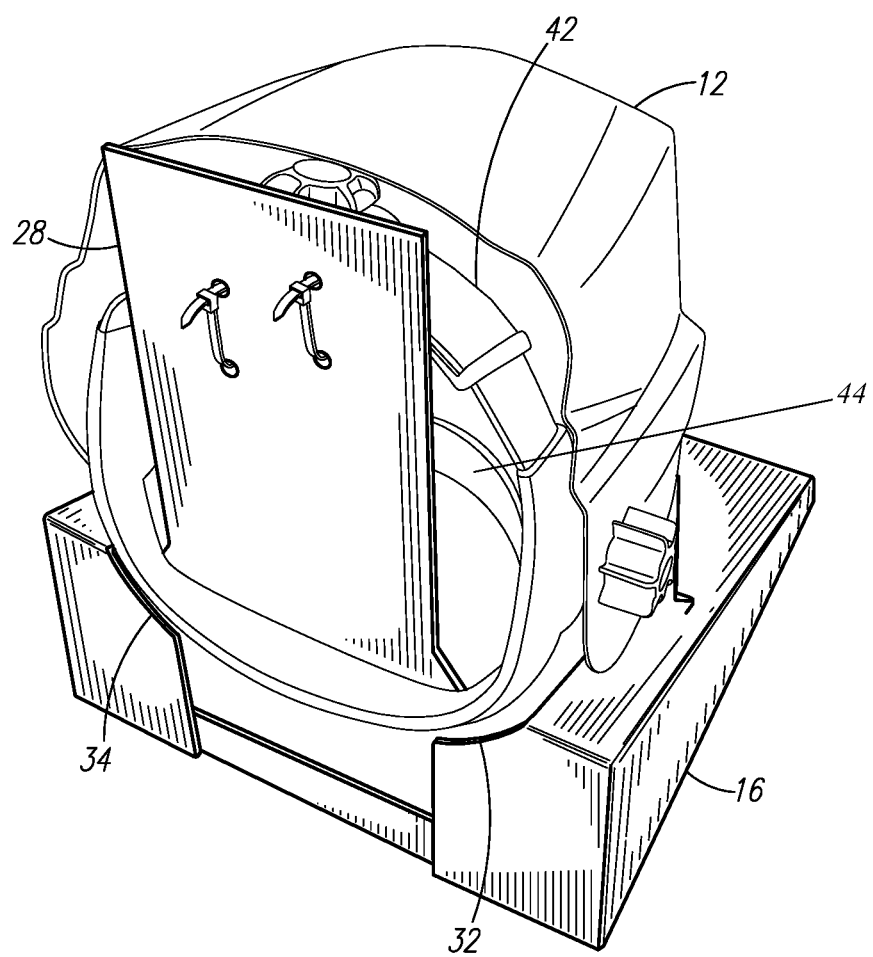
FIG. 6 is another perspective view of a portion of a container for a welding helmet.

FIG. 6 is a rear perspective view of the welding helmet 12 placed into the insert wedge 16. The welding helmet 12 includes headgear comprising a headband 42 and cross member 44 that extends between opposite sides of the headband (e.g., from left to right or front to back). When the welding helmet 12 is worn, the headband 42 is rotated to project rearward from the interior of the welding helmet and is oriented generally perpendicularly to the welding helmet. The headband 42 wraps around the circumference of a user's head when worn, and the cross member 44 extends between opposite sides of the headband and across the top of the user's head. In FIG. 6, the headband 42 has been rotated to a generally vertical storage position within the welding helmet.

The slots 32, 34 on either side of the tongue portion 28 allow the headband 42 to project downward through the slots into the main body of the insert wedge 16 when the headgear is in the storage position. It can be seen that the headband 42 passes through both slots 32, 34 and extends beneath the fold in the tongue portion 28. The part of the headband 42 that projects downward into the insert wedge 16 can be the front part of the headband that is adjacent to the forehead of a user when the helmet is worn.

The tongue portion 28 is routed through the headgear, to provide another security feature. In particular, the tongue portion 28 is routed between the cross member 44 and the headband 42. The tongue portion 28 projects from a central region enclosed by the headband 42 and is folded upward against the back of the welding helmet 12 to a generally vertical position parallel with the headband. The tongue portion 28 is then tied or otherwise attached to the welding helmet 12 at an upper portion of the welding helmet. In particular, the tongue portion 28 can be tied to the headband 42 through the apertures 30 in the distal end tongue portion using zip-ties or similar security structure. In this manner the welding helmet 12 can be physically secured and locked into to the insert wedge 16 so that the welding helmet cannot be separated from the insert wedge without either cutting the ties or damaging (e.g., tearing) the insert wedge.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A container for a welding helmet comprising a headband and a lens, said container comprising:
   an outer box; and
   a removable insert wedge that is removable from the outer box, the removable insert wedge comprising a tongue portion extending through the headband of the welding helmet and attached to the welding helmet,
   wherein the outer box forms an opening in at least one vertical side of the outer box, thereby enabling the welding helmet and the lens of the welding helmet to be accessed from outside of the outer box through the opening, and wherein the opening is sized to prevent removal of the insert wedge and attached welding helmet through the opening without damaging the outer box.

2. The container of claim 1, wherein the outer box comprises a hinged access panel allowing concurrent removal of the welding helmet and attached insert wedge from the outer box.

3. The container of claim 1, wherein the insert wedge includes respective slots adjacent to the tongue portion, and a portion of the headband projects into the insert wedge beneath the tongue portion through the respective slots.

4. The container of claim 3, wherein the respective slots are adjacent to a proximal end of the tongue portion, and a distal end of the tongue portion is attached to the headband.

5. The container of claim 1, wherein the tongue portion comprises an upward fold and is attached to the welding helmet at an upper portion of the welding helmet.

6. The container of claim 5, wherein the headband is rotatable within the welding helmet to a storage position within the welding helmet, and the tongue portion is attached to the headband at said upper portion of the welding helmet.

7. The container of claim 6, wherein the headband comprises a cross member that extends between opposite sides of the headband, and the tongue portion extends between the cross member and the headband to project from of a central region enclosed by the headband.

8. The container of claim 1, wherein the outer box forms a further opening in another vertical side of the outer box, thereby enabling a shade adjustment knob of the welding helmet to be accessed from outside of the outer box through the further opening.

9. The container of claim 1, wherein the insert wedge forms a central depression for nesting the welding helmet within the insert wedge, and a forwardly-projecting spatter guard on the welding helmet projects beneath an upper surface of the insert wedge when the welding helmet is nested within the insert wedge.

10. The container of claim 9, wherein the central depression is formed by a cut portion, in the upper surface of the insert wedge, that is folded inwardly into the insert wedge.

11. A container for a welding helmet, comprising:
    an outer box; and
    a removable insert wedge that is removable from the outer box, the removable insert wedge comprising a tongue portion extending through a headband of the welding helmet, wherein the insert wedge includes respective slots adjacent to the tongue portion that allow the headband to project into the insert wedge beneath the tongue portion, and the tongue portion is attached to the headband, and wherein the insert wedge forms a central depression for nesting the welding helmet within the insert wedge, and a forwardly-projecting spatter guard on the welding helmet projects beneath an upper surface of the insert wedge when the welding helmet is nested within the insert wedge, and
    wherein the outer box forms an opening in at least one vertical side of the outer box, thereby enabling the welding helmet and a lens of the welding helmet to be accessed from outside of the outer box through the opening, and wherein the opening is sized to prevent removal of the insert wedge and attached welding helmet through the opening without damaging the outer box.

12. The container of claim 11, wherein the tongue portion comprises an upward fold, and extends along a central region enclosed by the headband.

13. The container of claim 12, wherein the upward fold in the tongue portion is located between the respective slots adjacent to the tongue portion.

14. The container of claim 11, wherein the outer box forms a further opening in another vertical side of the outer box, said further opening being aligned with a shade adjustment knob of the welding helmet.

15. The container of claim 11, wherein the respective slots are adjacent a proximal end of the tongue portion, and the tongue portion comprises an upward fold, and a distal end of the tongue portion is tied to the headband.

16. The container of claim 11, wherein the central depression is formed by a cut portion, in the upper surface of the insert wedge, that is folded inwardly into the insert wedge.

17. A container for a welding helmet, comprising:
an outer box comprising a hinged access panel;
a insert wedge that is removable from the outer box; and
a helmet attachment tongue extending from the insert wedge and having a proximal end attached to the insert wedge and a distal end,
wherein the welding helmet comprises a headband that is rotatable within the welding helmet to a storage position, and with the headband in the storage position, the helmet attachment tongue extends through the headband and extends upward along a central region enclosed by the headband and the distal end of the helmet attachment tongue is attached to the headband at an upper portion of the welding helmet, and the insert wedge includes respective slots adjacent to the proximal end of the helmet attachment tongue and a lower portion of the headband projects into the insert wedge through the respective slots and beneath the helmet attachment tongue, wherein:

the insert wedge forms a central depression for nesting the welding helmet within the insert wedge, and a forwardly-projecting spatter guard on the welding helmet projects beneath an upper surface of the insert wedge when the welding helmet is nested within the insert wedge, and the central depression is formed by a cut portion, in the upper surface of the insert wedge, that is folded inwardly into the insert wedge, the outer box forms an opening in at least one vertical side of the outer box, thereby enabling the welding helmet and a lens of the welding helmet to be accessed from outside of the outer box through the opening, and the opening is sized to prevent removal of the insert wedge and attached welding helmet through the opening without damaging the outer box, and the welding helmet and attached insert wedge are removable from the outer box without damaging the outer box when the access panel is in an open position.

18. The container of claim 17, wherein the headband comprises a cross member that extends between opposite sides of the headband, and the helmet attachment tongue extends between the cross member and the headband to project from of the central region enclosed by the headband.

* * * * *